United States Patent
Ranucci et al.

(10) Patent No.: US 9,615,830 B2
(45) Date of Patent: Apr. 11, 2017

(54) SURGICAL FASTENER

(71) Applicant: C.R. Bard, Inc., Murray Hill, NJ (US)

(72) Inventors: Kevin J. Ranucci, Warwick, RI (US); Saurav V. Gupta, Medway, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 75 days.

(21) Appl. No.: 14/075,441

(22) Filed: Nov. 8, 2013

(65) Prior Publication Data

US 2015/0133971 A1   May 14, 2015

(51) Int. Cl.
| | |
|---|---|
| *A61B 17/08* | (2006.01) |
| *A61B 17/064* | (2006.01) |
| *A61B 17/068* | (2006.01) |
| *A61B 17/00* | (2006.01) |
| *A61B 90/00* | (2016.01) |

(52) U.S. Cl.
CPC ........... *A61B 17/08* (2013.01); *A61B 17/064* (2013.01); *A61B 17/068* (2013.01); *A61B 2017/00477* (2013.01); *A61B 2017/00526* (2013.01); *A61B 2017/0649* (2013.01); *A61B 2090/0807* (2016.02); *Y10T 29/49826* (2015.01)

(58) Field of Classification Search
CPC ............. A61B 17/08; A61B 2017/0649; F16B 25/0005; Y10T 29/49881
USPC ......................................... 29/240.5; 411/383
See application file for complete search history.

(56) References Cited

U.S. PATENT DOCUMENTS

| | | | |
|---|---|---|---|
| 2,407,879 A | * | 9/1946 | Haas ................. F16B 37/12 411/438 |
| 3,229,374 A | * | 1/1966 | Comorau ................. G01B 3/40 29/240.5 |
| 4,762,453 A | | 8/1988 | DeCaro |
| 4,917,554 A | | 4/1990 | Bronn |
| 5,904,696 A | | 5/1999 | Rosenman |
| 6,383,187 B2 | | 5/2002 | Tormala et al. |
| 6,409,445 B1 | | 6/2002 | Beale et al. |
| 7,189,251 B2 | | 3/2007 | Kay |
| 7,862,573 B2 | | 1/2011 | Darois et al. |
| 7,867,252 B2 | | 1/2011 | Criscuolo et al. |

(Continued)

FOREIGN PATENT DOCUMENTS

| | | |
|---|---|---|
| EP | 0 663 184 A1 | 7/1995 |
| GB | 2417208 | 2/2006 |

(Continued)

OTHER PUBLICATIONS

U.S. Appl. No. 15/246,888, filed Aug. 25, 2016, Ranucci et al.

(Continued)

*Primary Examiner* — Thomas McEvoy
(74) *Attorney, Agent, or Firm* — Wolf, Greenfield & Sacks, P.C.

(57) ABSTRACT

A surgical fastener is provided for various surgical fastening applications, including attaching an implantable prosthesis, such as a soft tissue repair fabric, to tissue and/or muscle. The surgical fastener may include a coil body and a separate head that is attached to the coil body. The head may include an internal thread that is threadably attached to the coil body. The head may also be further secured to the coil body with a compression fit therebetween. A locking feature may prevent back-out of the coil body from the head. The surgical fastener may be assembled by threading the coil body through the head.

28 Claims, 6 Drawing Sheets

(56) References Cited

U.S. PATENT DOCUMENTS

| | | | |
|---|---|---|---|
| 8,087,142 B2 | 1/2012 | Levin et al. | |
| 8,231,639 B2 | 7/2012 | Bolduc et al. | |
| 8,292,933 B2 | 10/2012 | Zergiebel | |
| 8,343,176 B2 | 1/2013 | Criscuolo et al. | |
| 8,382,778 B2 | 2/2013 | Criscuolo et al. | |
| 9,072,511 B2* | 7/2015 | Tegzes | A61B 17/0401 |
| 2003/0181913 A1 | 9/2003 | Lieberman | |
| 2004/0193217 A1 | 9/2004 | Lubbers et al. | |
| 2005/0187568 A1 | 8/2005 | Klenk et al. | |
| 2007/0038220 A1 | 2/2007 | Shipp | |
| 2007/0088390 A1 | 4/2007 | Paz et al. | |
| 2007/0140810 A1* | 6/2007 | Itou | F16B 37/12 411/251 |
| 2007/0250064 A1 | 10/2007 | Darois et al. | |
| 2010/0010520 A1* | 1/2010 | Takahashi | A61B 17/064 606/157 |
| 2010/0256690 A1 | 10/2010 | Appenzeller et al. | |
| 2010/0274266 A1 | 10/2010 | Rimer et al. | |
| 2011/0087240 A1 | 4/2011 | Shipp | |
| 2011/0092992 A1 | 4/2011 | Darois et al. | |
| 2011/0295282 A1 | 12/2011 | Glick et al. | |
| 2011/0295319 A1 | 12/2011 | Duplessis et al. | |
| 2012/0022557 A1 | 1/2012 | Cabiri et al. | |
| 2012/0101526 A1 | 4/2012 | Bennett | |
| 2013/0131700 A1 | 5/2013 | Criscuolo et al. | |
| 2014/0243855 A1 | 8/2014 | Sholev et al. | |
| 2015/0133964 A1 | 5/2015 | Ranucci et al. | |
| 2015/0133970 A1 | 5/2015 | Ranucci et al. | |
| 2015/0133972 A1 | 5/2015 | Ranucci et al. | |
| 2015/0152908 A1* | 6/2015 | Schwarzbich | F16B 37/12 470/14 |

FOREIGN PATENT DOCUMENTS

| | | |
|---|---|---|
| WO | WO 97/07744 A1 | 3/1997 |
| WO | WO 02/09625 A1 | 2/2002 |
| WO | WO 2005/004727 A1 | 1/2005 |
| WO | WO 2005/081936 A2 | 9/2005 |
| WO | WO 2011/092692 A2 | 8/2011 |
| WO | WO 2012/176195 A2 | 12/2012 |
| WO | WO 2013/046115 A1 | 4/2013 |

OTHER PUBLICATIONS

[No Author Listed], Winding. (n.d.). Dictionary.com Unabridged. Retrieved Apr. 14, 2016 from Dictionary.com website. 12 Pages. Http://www.dictionary.com/browse/winding.

U.S. Appl. No. 14/075,398, filed Nov. 8, 2013, Ranucci et al.
U.S. Appl. No. 14/075,464, filed Nov. 8, 2013, Ranucci et al.
U.S. Appl. No. 14/075,354, filed Nov. 8, 2013, Ranucci et al.

* cited by examiner

A-A

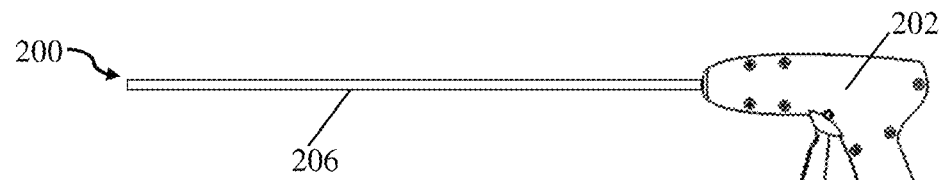
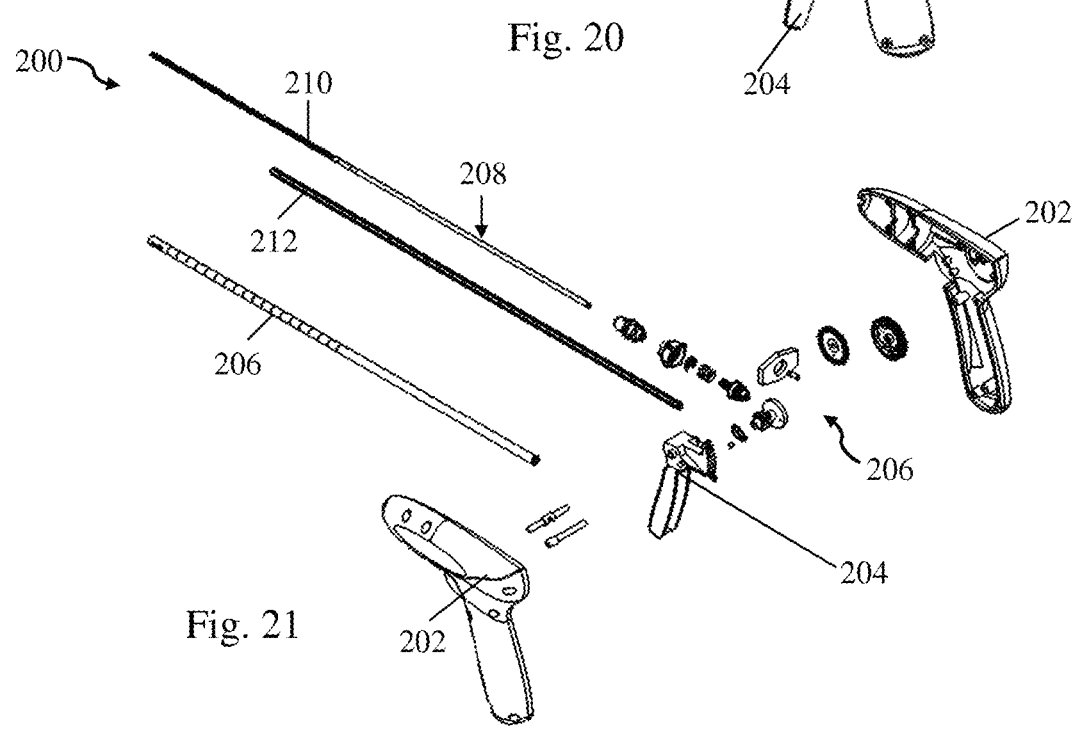
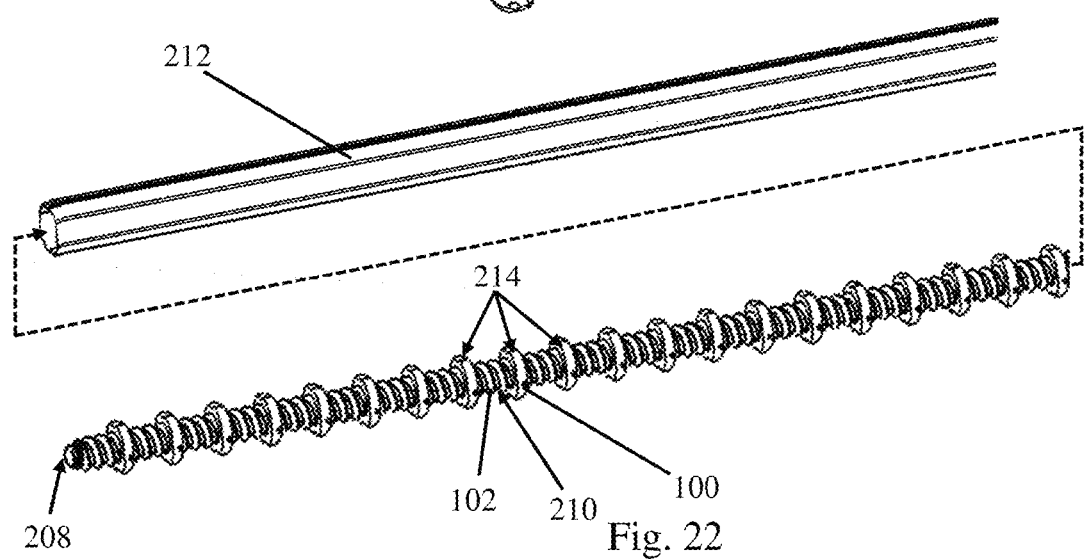

SURGICAL FASTENER

FIELD

Disclosed embodiments are related to a surgical fastener, and more particularly, to a surgical fastener that includes a coil body with an attached head.

BACKGROUND

Surgical fasteners are widely used in many different medical procedures. For example, staples, sutures, clips and other fasteners are commonly used in laparoscopic and open surgical procedures.

SUMMARY

In one aspect of the invention, a surgical fastener comprises a coil body and a separate head that is attached to the coil body. The coil body includes a plurality of coil windings and has a proximal end and a distal end. The head includes a through hole with an internal thread that is threadably attached to the coil body.

In another aspect of the invention, a surgical fastener comprises a coil body, a separate head that is attached to the coil body, and at least one locking feature that secures the head to the coil body. The coil body includes a plurality of coil windings and has a proximal end and a distal end. The head includes a through hole adapted to receive a guide rod of a delivery device. The coil body is attached to the head by a compression fit.

In another aspect of the invention, a method of assembling a surgical fastener comprises threading a coil body that includes a plurality of coil windings through a separate head, and securing the coil body to the head with a portion of the coil body extending from a proximal face of the head.

BRIEF DESCRIPTION OF DRAWINGS

Various embodiments of the invention will now be described, by way of example, with reference to the accompanying drawings, in which:

FIG. 20 is a schematic side view of a laparoscopic delivery device;

FIG. 21 is a schematic exploded perspective view of the laparoscopic delivery device of FIG. 20; and FIG. 22 is a schematic exploded perspective view of the stationery mandrel and rotatable cannula.

DETAILED DESCRIPTION

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

A surgical fastener is provided for various surgical fastening applications. For example, the surgical fastener may be used to attach an implantable prosthesis, such as a soft tissue repair fabric, to tissue and/or muscle. Other non-limiting applications for the fastener may involve joining portions of tissue and/or muscle together, joining portions of tissue and/or muscle to bone, and/or joining an implantable prosthesis to bone.

In one embodiment, a surgical fastener may include a coil body and a separate head that is attached to the coil body. This arrangement may improve the manufacturability of the fastener and reduce costs, particularly as compared to costs associated with injection molding a complex surgical fastener. This arrangement may be particularly suited for manufacturing the head and coil body from different materials.

Figure 1:
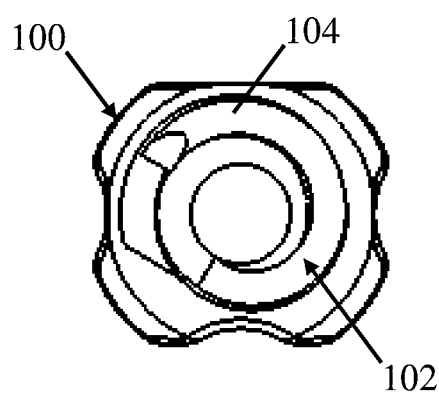
FIG. 1 is a schematic top view of a surgical fastener.
Figure 2:
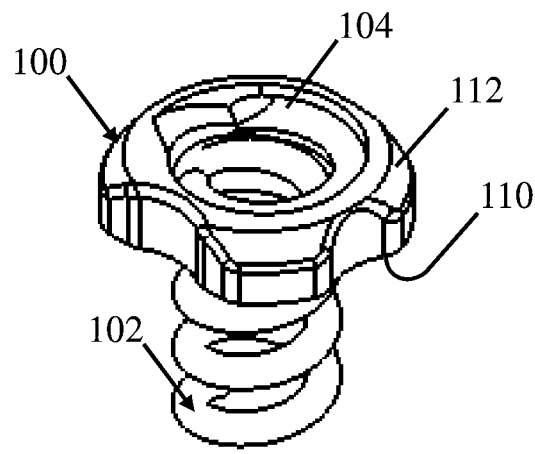
FIG. 2 is a schematic perspective view of the surgical fastener of FIG. 1.
Figure 3:
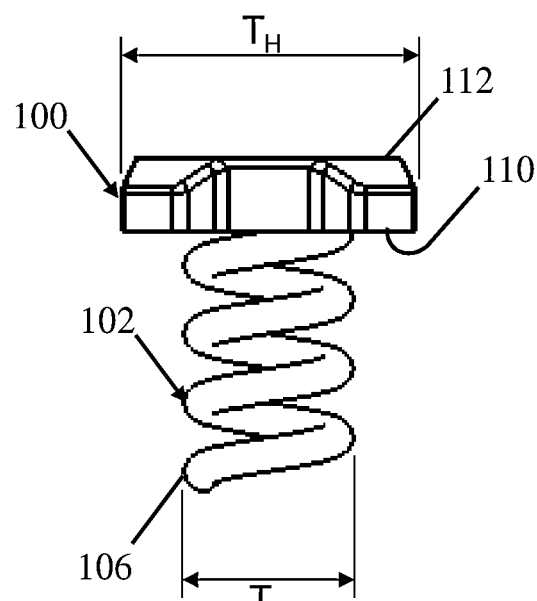
FIG. 3 is a schematic front view of the surgical fastener of FIG. 1.
Figure 4:
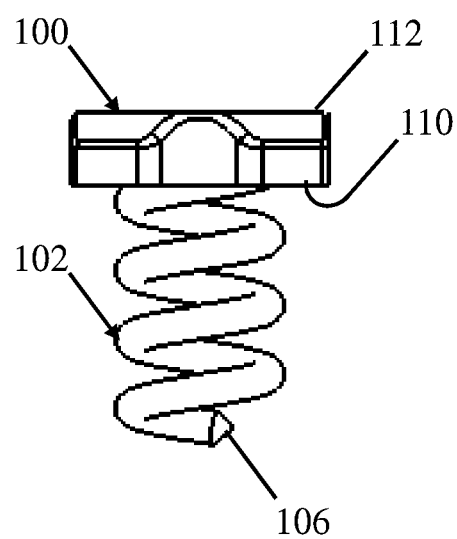
FIG. 4 is a schematic side view of the surgical fastener of FIG. 1.
Figure 5:
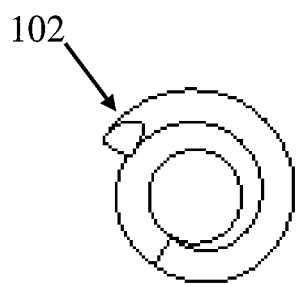
FIG. 5 is a schematic top view of a surgical fastener coil body.
Figure 6:
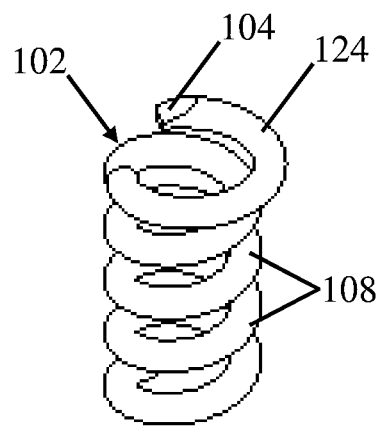
FIG. 6 is a schematic perspective view of the surgical fastener coil body of FIG. 5.
Figure 7:
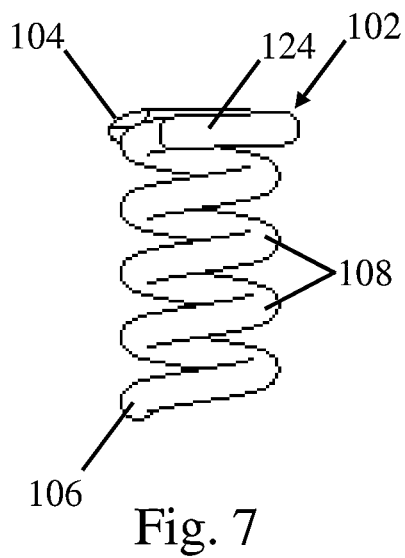
FIG. 7 is a schematic front view of the surgical fastener coil body of FIG. 5.
Figure 8:
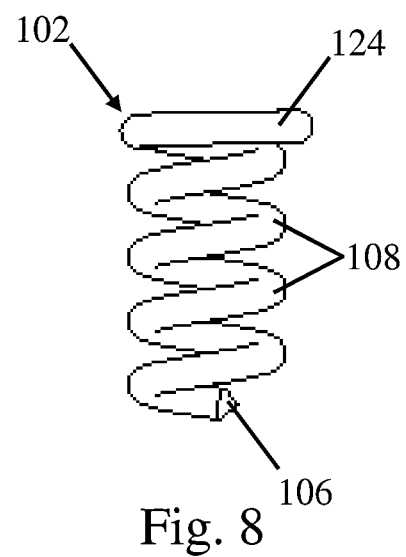
FIG. 8 is a schematic side view of the surgical fastener coil body of FIG. 5.
Figure 9:
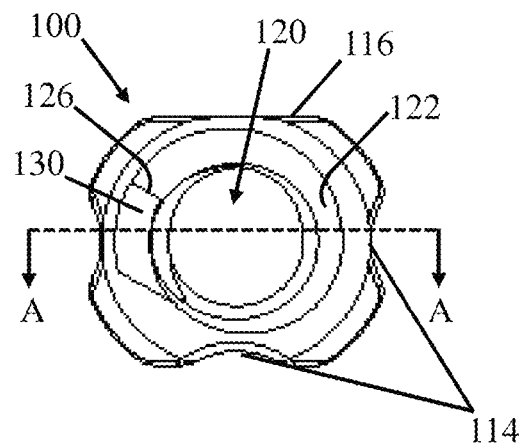
FIG. 9 is a schematic top view of a surgical fastener head.
Figure 10:
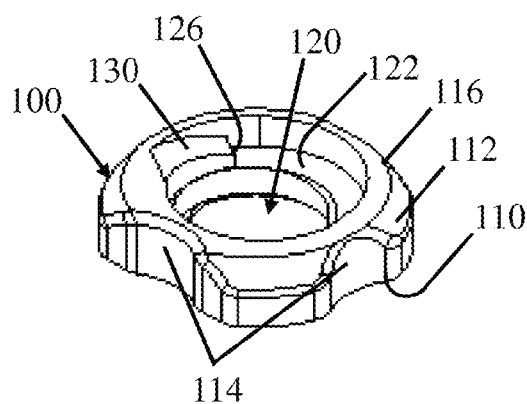
FIG. 10 is a schematic perspective view of the surgical fastener head of FIG. 9.
Figure 11:
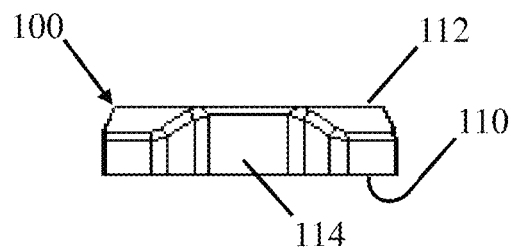
FIG. 11 is a schematic front view of the surgical fastener head of FIG. 9.
Figure 12:
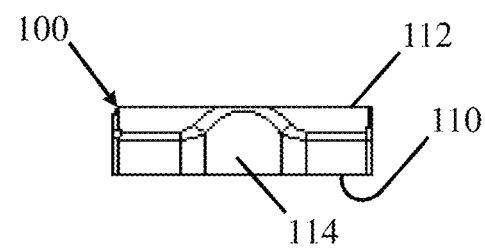
FIG. 12 is a schematic side view of the surgical fastener head of FIG. 9.

For the purposes of this application, a transverse dimension of the coil body or head generally refers to a dimension of the coil body or head within a plane that is perpendicular to a long axis of the surgical fastener when it is assembled (e.g. a diameter of a cylindrical coil body, a width of a rectangular head, the length of a side of a triangular coil body, etc. . . . ). For example, an outer transverse dimension of the coil body would refer to the lateral distance between opposing outer surfaces of the coil body and an inner transverse dimension of the coil body would refer to the lateral distance between opposing interior surfaces of the coil body. The outer transverse dimensions of the head $T_H$ and coil body $T_C$ in one embodiment are illustrated in FIG. 3 and correspond to the width of the head and the diameter of the coil body. It should be noted that in embodiments in which the head and/or the coil body are noncircular, the head and/or coil body may have both minimum and maximum transverse dimensions.

In some embodiments, a coil body may be configured to receive therethrough a guide mandrel of a delivery device and, for some applications, to mate with a corresponding external thread on the guide mandrel. The head may also be configured to have a transverse dimension that is larger, such as wider or greater in diameter, than an outer transverse dimension of the coil body to engage and secure underlying material and/or tissue. The head may include one or more features that cooperate with corresponding features of a delivery device for driving the fastener from the device and into an implantable prosthesis and/or tissue, bone, or muscle.

Depending on the embodiment, the head may include an internal thread that is threaded to the coil body and attaches the head to a proximal end of the coil body. The head may also be secured to the coil body with a compression or press fit between the head and a portion of the coil body. The portion of the coil body may be located at a proximal end thereof. The head may include a cavity, such as a counterbore to a through hole, that receives the portion of the coil body therein to provide the compression or press fit. More specifically, the portion of the coil body received in the cavity may have an outer transverse dimension in a relaxed state that is larger than, or equal to, a transverse dimension of the cavity to create the compression or press fit as the coil body is threaded to the head. The portion of the coil body received in the cavity may include approximately a half turn or more of at least one coil. It should be understood that other locations and ways of providing a compression or press fit between the coil body and head might be used.

In addition to the coil body possibly being attached to the head with a compression or press fit between the head and a portion of the coil body, and/or being threaded together, in some embodiments, a locking feature may secure the head to the coil body, for example, to prevent back-out of the coil body from the head. In one embodiment, a locking feature may include a recess located on the head and a hook located at the proximal end of the coil body that engages the recess to secure the head to the coil body. In another embodiment, a locking feature may include an abutment located on the head that is engaged by a proximal end of the coil body to secure the head to the coil body. The head may include a ramp to guide the coil body into the head with the locking feature being located at an end of the ramp. Other types of locking features are contemplated as the current disclosure is not so limited.

In some embodiments, a surgical fastener may be assembled by threading the coil body to the head, and in some embodiments, a coil body may also be secured to the head to avoid backing out and/or rotation of the coil body relative to the head in an appropriate fashion. In such an embodiment, the distal end of the coil body, which may be configured to penetrate an implantable prosthesis, bone, muscle and/or tissue, may be inserted into and threaded through the proximal end of the head until at least a portion of a coil at the proximal end of the coil body engages with and becomes secured to the head. Alternatively, in some embodiments, such as when there is no corresponding threading on the head, at least a portion of the coil body may be compressed and inserted into the head and released to secure the coil body to the head.

In one illustrative embodiment shown in FIGS. 1-4, the surgical fastener may include a coil body 102 and a separate head 100 that is attached to a proximal end of the coil body 104. The distal end of the coil body 106 may be configured for penetrating an implantable prosthesis, tissue, muscle, and/or bone. In one embodiment, the distal end 106 may include a sharp distal tip, although the distal end may employ any suitable configuration as should be appreciated by one of skill in the art.

As depicted in FIGS. 5-8, the coil body 102 includes a plurality of coil windings 108. As illustrated, the coil windings 108 may be arranged in a helical or spiral configuration suitable for driving the fastener into and through prosthetic material, tissue, muscle and/or bone. Thus, the coil body may be cylindrical in shape with a circular cross-section, though other cross-sectional shapes such as triangular, rectangular, or any other appropriate shape also are contemplated. The coil body 102 may include any number of coil windings 108 with any desired spacing or pitch between the coil windings and any transverse dimension, including outer and inner transverse dimensions, suitable for a particular application as should be appreciated by one of skill. In one embodiment, the coil body may include coil windings having the same transverse dimension. However, if desired, one or more of the coil windings may have different transverse dimensions relative to each other. For example, the coil body may employ coil windings that decrease in size from the proximal end toward the distal end to form a coil body with a conical or tapered shape.

The head 100 may have any suitable configuration desired for a particular application, see FIGS. 1-4 and 9-13. In one embodiment, the head 100 includes, but is not limited to, a generally flat distal face 110 from which extends the coil body 102. The opposite or proximal face 112 of the head may have one or more generally flat, round, angled, and/or beveled surfaces, or combinations thereof, as should be apparent to one of skill.

To facilitate rotation of the fastener, the head 100 may include one or more drive features 114 that may be engaged by a drive member of a delivery device to rotate the head 100, and thereby rotate the fastener including the coil body 102. As best shown in FIGS. 9-13, the head may include one or more drive features 114 corresponding to one or more indents, depressions, or recesses along its outer periphery that are configured to receive and engage a corresponding feature of a drive member, such as one or more longitudinal internal ribs of a rotatable outer tube or cannula, of the delivery device. However, it is to be appreciated that the head may include any number of drive features with any suitable configuration as should be apparent of one of skill.

To facilitate orientation of the fastener within a delivery device, the head may include one or more alignment features 116 that coact with a corresponding feature of the delivery device to ensure proper orientation of the fastener. In the embodiment shown in FIGS. 9-13, the one or more alignment features 116 correspond only to one side of the head 100 having a generally flat configuration and free of a drive feature so that the fastener can only be inserted into the delivery device with the head 100 oriented in a particular direction relative to a drive member of the delivery device, not depicted. In this manner, the delivery device may be loaded with a stack of fasteners that are oriented with their distal tips located at the same angular position relative to each other for delivery and insertion. It is to be appreciated that an alignment feature 116 is not required, but if desired, the head may include any number of alignment features with any suitable configuration as should be apparent to one of skill.

Figure 13:
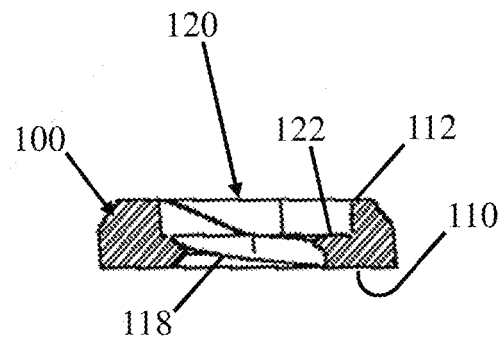
FIG. 13 is a schematic cross-sectional view of the surgical fastener head of FIG. 9.
Figure 15:
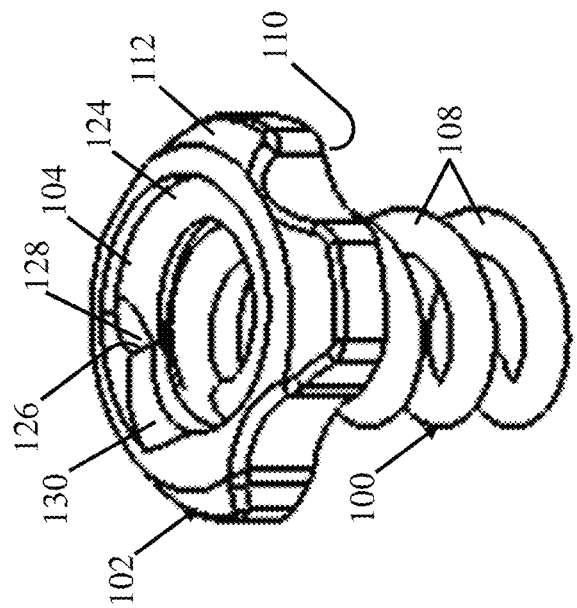
FIG. 15 is a schematic perspective view of the surgical fastener coil body and head of FIG. 14 in the assembled state.
Figure 14:
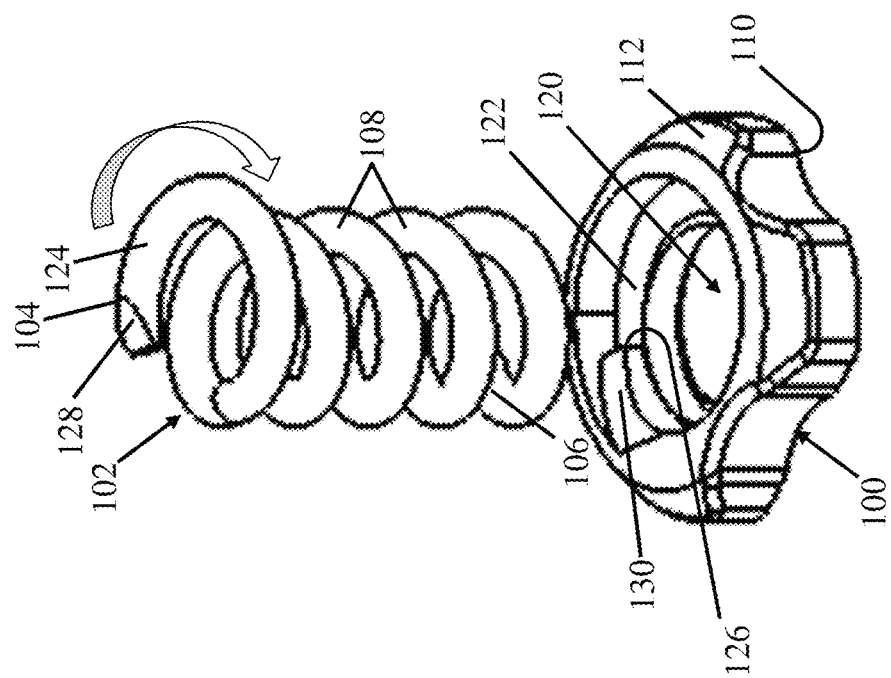
FIG. 14 is schematic perspective view of a surgical fastener coil body and head being assembled.
Figure 16:
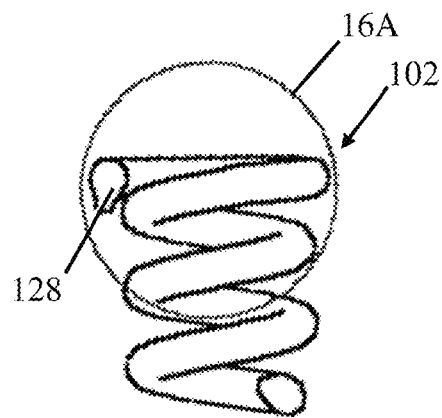
FIG. 16 is a schematic front view of a surgical fastener coil body.
Figure 16A:
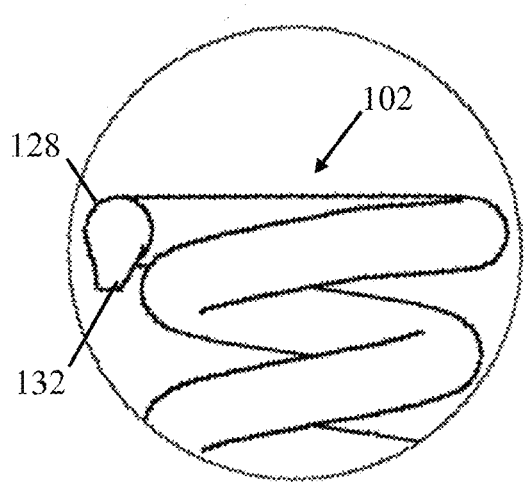
FIG. 16A is a schematic enlarged view of the surgical fastener coil body of FIG. 16.
Figure 17:
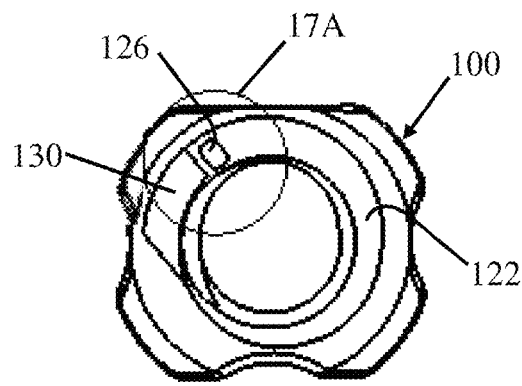
FIG. 17 is a schematic top view of a surgical fastener head.
Figure 17A:
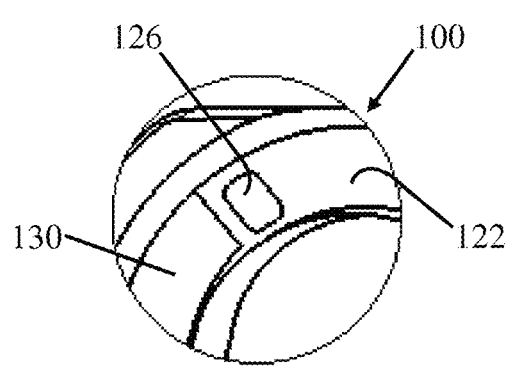
FIG. 17A is a schematic enlarged view of the surgical fastener head of FIG. 17.
Figure 18:
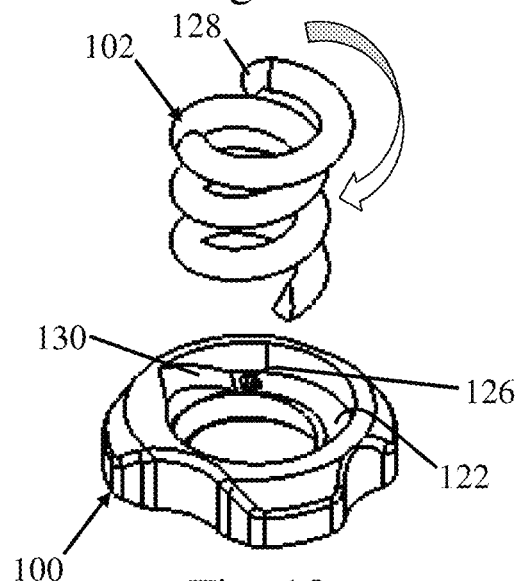
FIG. 18 is a schematic perspective view of a surgical fastener coil body and head being assembled.
Figure 19:
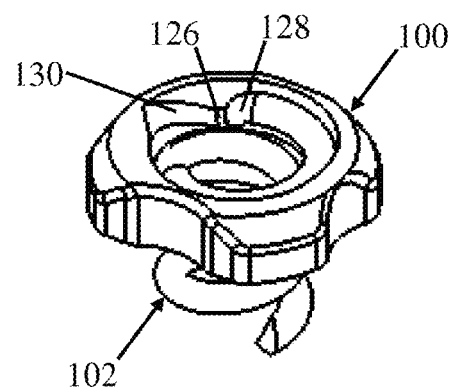
FIG. 19 is a schematic perspective view of the surgical fastener coil body and head of FIG. 18 in the assembled state.

In one embodiment, the head 100 may be attached to the coil body 102 by threading the coil body and head together. As illustrated in FIG. 13, the head 100 may include an internal thread 118 that corresponds to and is threaded to the coil body 102 as depicted in FIGS. 14-15 and 18-19. As shown in the figures, the internal thread 118 may be located in a through hole 120 that extends through the head 100. The coil body 102 may be attached to the head 100 by inserting the distal end of the coil body 106 into the through hole 120 in a distally directed direction from the proximal face of the head 112 and rotating the coil body 102 and/or the head 100, as indicated by the arrow, to thread the components together until the proximal end of the coil body 104 is positioned at or within the head 100. Alternatively, in some embodiments, the proximal end of the coil body 104 might be inserted into the through hole 120 from the distal face of the head 110 to assemble the head 100 and coil body 102. Depending on the embodiment, overthreading of the coil body 102 relative to the head 110 during assembly may be prevented by controlling the amount of rotation during assembly. Alternatively, when appropriate interlocking features or interferences may be used to control the assembly, and overthreading of the coil body 102 relative to the head 110 may be prevented by monitoring an assembly force or torque threshold. Other methods of preventing overthreading are also possible.

As noted above, the coil fastener may employ a variety of arrangements for further securing of the head to the coil body to prevent backout and/or rotation of the components after threading them together or otherwise attaching them. For example, in one embodiment, the head may be secured to the coil body using a compression fit between the head and a portion of the coil body, such as a portion of at least one coil winding, although other suitable arrangements may be employed to secure the head to the coil body. It should be understood that a compression fit could also be used without threads to both attach and secure the coil body to the head. The compression fit may also help prevent overthreading of the coil body relative to the head because the assembly torque will increase when the coil winding corresponding to the compression fit portion of the coil body begins to engage with the threads.

One embodiment of a compression fit is illustrated in FIGS. 9-13. As illustrated in the figures, the head 100 may include a cavity 122 extending inwardly from the proximal face 112 that is larger than the through hole 120. In this manner, the cavity 122 may be in the form of a counterbore located proximal to the through hole, although other suitable arrangements may be utilized. A proximal-most coil winding 124, or a portion thereof, located at the proximal end 104 of the coil body 102 has an outer transverse dimension that is larger than a transverse dimension of the cavity 122 and may also be larger than the outer transverse dimensions of the other coil windings 108, see FIGS. 5-8 and 10-14. In one embodiment, the proximal-most coil winding 124 may include approximately a half turn or more of a coil winding. As the coil body 102 is threaded, or otherwise positioned, into the head 100, the proximal-most coil winding 124 will become radially compressed inwardly as it enters the cavity 122 to create a compression or otherwise snug fit, such as a friction fit, between the coil and the cavity wall to secure the head 100 and coil body 102 together. The proximal-most coil winding 124 may also engage the bottom of the cavity 122 to position the coil body relative to the head 100 and prevent the coil body 102 from being threaded through the head. If desired, more than one coil winding may be compressed into the head 100 to secure the head 100 and the coil body 102 together.

The coil fastener may employ an additional arrangement to further secure the head to the coil body to prevent the coil body from being backed out of the head after it has been fully assembled. For example, in one embodiment, the head may include a locking feature that engages a corresponding portion of the coil body to fully secure the components together.

In one illustrative embodiment shown in FIGS. 9-15, a head 100 may include a locking feature 126 such as an abutment located within the cavity 122 that engages with the proximal tip 128 of the coil body to avoid back-out of the coil body 102 when the coil body is fully threaded into the head 100. To guide and facilitate engagement between the locking feature 126 and the proximal tip 128 of the coil body, the head 100 may include a ramp 130 or other ramp-like feature within the cavity 122 that guides the proximal-most coil winding into the cavity and towards the locking feature 126. The ramp 130 may be configured to terminate above the bottom of the cavity 122 to form the noted abutment at the end of the ramp.

In another embodiment as shown in FIGS. 16-19, a head 100 may include a locking feature 126 such as a recess or notch at a peripheral location of the bottom of the cavity 122 and the coil body 102 may include a hook 132 or hook-like feature at the proximal tip 128 that engages the recess, or other locking feature 126, when the coil body 102 is fully threaded into the head 100. When the hook 132 is engaged with the recess or notch, or other locking feature 126, the components are locked together and back-out of the coil body 102 from the head 100 due to the rotational force applied to the coil body during deployment is prevented. To guide and facilitate engagement between the locking features, the head 100 may again include a guide, such as a ramp 130 or other ramp-like feature, located within and extending to the bottom of the cavity 122 that guides the proximal-most coil winding 124 into the cavity 122 and the hook 132 into the locking feature 126 which is located adjacent the lower end of the ramp 130.

In one embodiment, a hook 132 may be integrally formed with the coil body by forming, such as by bending, the proximal tip of the proximal-most coil into a desired configuration suitable for engaging the recess. Alternatively, if desired, a separately manufactured locking feature may be attached to the proximal tip of the coil body in any suitable manner as should be apparent to one of skill in the art.

In one embodiment, a surgical fastener may include a coil body having a length of approximately 3 mm to approximately 6.5 mm extending from the distal face of the head. The coil body may include approximately 2.5 turns to approximately 6 turns of coil windings having an outer transverse dimension of approximately 2.5 mm to approximately 4.9 mm (0.098 inches to 0.193 inches), for delivery through a 5 mm cannula, with a pitch of approximately 0.7 mm to approximately 1.1 mm (0.03 to 0.045 inches). The proximal-most coil winding may have about 0.5 to 1 turns with a relaxed outer transverse dimension of approximately 2.9 mm (0.115 inches) for insertion into a head cavity having a transverse dimension of approximately 2.8 mm (0.110 inches) to approximately 2.85 mm (0.112 inches) to create a compression fit between the coil winding and the head. The head may also include an internal thread that corresponds to the coil body for threading the components together. The head may have an outer transverse dimension of approximately 2.7 mm to approximately 4.98 mm (0.106 inches to 0.196 inches) and a thickness of approximately 0.97 mm (0.030 inches) to approximately 1.02 mm (0.04 inches) with a cavity depth between approximately 0.46 mm (0.018 inches) to 0.64 mm (0.025 inches). Of course, the surgical fastener may employ a coil body and head having any suitable sizes and configurations for a desired application as should be apparent to one of skill in the art.

The surgical fastener may be made from one or more biocompatible materials that are suitable for a particular surgical application and is sterilized or sterilizable. Additionally, the fastener components may be made from a non-absorbable material, an absorbable material or a combination of absorbable and non-absorbable materials. The components may also be made from, and/or coated with, materials and/or include features that may resist tissue ingrowth and/or adhesions, permit tissue ingrowth and/or adhesions, or a combination thereof. The components may be made from metal, plastic and/or any other suitable biocompatible materials as should be apparent to one of skill in the art.

In one embodiment, the head may be made from a plastic polymer including, but not limited to, polyether ether ketone (PEEK) or acetal, and the coil body may be made from a metal including, but not limited to, stainless steel, nitinol, or titanium. If desired, the head alone or the head and the coil body may be made from an absorbable metal and/or polymer. While specific materials are noted above, any appropriate combination of materials could be used for the head and coil body.

In one exemplary embodiment, the surgical fastener may have an overall length of approximately 4.5 mm with a coil length extending from the head of approximately 3.5 mm. The head also has a thickness of approximately 1 mm and a transverse dimension of approximately 4.2 mm (0.164 inches). The coil body has an outer transverse dimension of approximately 2.7 mm (0.105 inches) and is formed of 0.46 mm (0.018 inch) metal wire to have a constant pitch of approximately 0.91 mm to 1.07 mm (0.036 inches to 0.042 inches). Other dimensions for the coil body and head are also possible.

The various embodiments of a surgical fastener may be delivered to a surgical site using a delivery device that imparts rotation to the fastener and drives the fastener into prosthetic material, tissue, muscle and/or bone. As shown in FIGS. 20-22, the delivery device 200 may include a handle 202 including a trigger 204 at a proximal end of the device. The delivery device 200 may also include an outer tube or cannula 206 extending in a distal direction from the handle 202 and a mandrel 208 that extends along the length of the outer tube or cannula 206 for supporting and/or guiding one or more fasteners 214 within the cannula. The mandrel 208 may include an external thread 210 that corresponds to and mates with the coil body 102 and/or head 100 of the one or more fasteners 218 to assist with delivery and installation of a distal most fastener with the delivery device 200. In some embodiments, the mandrel 208 is a stationary mandrel and a rotatable cannula 212, or other appropriate rotator, is configured and arranged to engage and rotate the head of each fastener. When the trigger 204 of the delivery device 200 is actuated a transmission 206 rotates the rotatable cannula 212 relative to the mandrel 208 thus rotating each fastener 214 about the mandrel 208. Rotation of the fasteners 214 about the threaded mandrel 208 in turn provides a reactive thrust to the fasteners causing the fasteners to be driven in a distal direction along the length of the mandrel 208, out of a distal end of the cannula 206, and into the prosthetic material and/or tissue.

While a laparoscopic delivery device has been depicted in the above figures, the current disclosure is not so limited. Instead, the currently disclosed surgical fasteners may be used with any appropriate device capable of deploying the disclosed surgical fasteners. For example, the surgical fasteners could also be used in other delivery devices such as an endoscopic device, a borescopic device, a catheter, a surgical instrument for use in "open" procedures, or any other appropriate surgical instrument.

It should be understood that the foregoing description of various aspects of at least one embodiment of the invention are intended merely to be illustrative thereof and that other embodiments, modifications, and equivalents of the invention are within the scope of the invention recited in the claims appended hereto. Accordingly, the foregoing description and drawings are by way of example only.

What is claimed is:

1. A surgical fastener comprising:
   a coil body including a plurality of coil windings, the coil body having a proximal end and a distal end; and
   a separate head that is attached and rotationally fixed relative to the coil body, the head including a through hole with an internal thread that is threadably fixed to at least a portion of a coil winding of the coil body, wherein the head includes at least one drive feature that is engageable by a drive member of a delivery device to rotate the head and coil body of the surgical fastener;
   wherein at least one of the plurality of coil windings extends distally from the head when the coil body is threadably fixed to the head.

2. The surgical fastener according to claim 1, wherein the coil body is further secured to the head by a compression fit between the head and a portion of the coil body.

3. The surgical fastener according to claim 2, wherein the portion of the coil body includes at least a half turn of a coil winding.

4. The surgical fastener according to claim 2, wherein the portion of the coil body is located at the proximal end thereof.

5. The surgical fastener according to claim 2, wherein the head includes a cavity that receives the portion of the coil body therein to secure the coil body to the head.

6. The surgical fastener according to claim 5, wherein the cavity is located proximal to the internal thread.

7. The surgical fastener according to claim 5, wherein the cavity has a traverse dimension that is larger than a transverse dimension of the through hole.

8. The surgical fastener according to claim 5, wherein the portion of the coil body has an outer transverse dimension in a relaxed state that is larger than a transverse dimension of the cavity to create a compression, or press, fit as the coil body is threaded to the head.

9. The surgical fastener according to claim 1, wherein the head includes a locking feature that engages the coil body to secure the head to the coil body.

10. The surgical fastener according to claim 9 wherein the locking feature includes a recess formed in the and the coil body includes a hook that engages the recess to secure the head to the coil body.

11. The surgical fastener according to claim 9, wherein the locking feature includes an abutment formed in the head that is engaged by the proximal end of the coil body to secure the head to the coil body.

12. The surgical fastener according to claim 11, wherein the head includes a guide adjacent the internal thread, the abutment being located at an end of the guide.

13. The surgical fastener according to claim 12, wherein the guide is a ramp.

14. The surgical fastener according to claim 1, wherein the coil body is constructed and arranged to mate with a corresponding external thread on a guide rod of a delivery device.

15. The surgical fastener according to claim 1, wherein the head is attached to a proximal portion of the coil body.

16. The surgical fastener according to claim 1, wherein the at least one drive feature is one or more recesses formed in the head.

17. The surgical fastener according to claim 16, wherein the head includes an outer periphery and the at least one drive feature is located at the outer periphery.

18. A surgical fastener comprising:
a coil body including a plurality of coil windings, the coil body having a proximal end and a distal end;
a separate head that is attached to the coil body, the head including a through hole adapted to receive a guide rod of a delivery device, the coil body being attached to the head with a compression or press fit therebetween; and
at least one locking feature that secures the head to the coil body, wherein the head includes at least one drive feature that is engageable by a drive member of a delivery device to rotate the surgical fastener, wherein a portion of the coil body has an outer transverse dimension in a relaxed state that is larger than a transverse dimension of a cavity of the head in which the portion of the coil body is received to create the compression or press fit with the head; and
wherein at least one of the plurality of coil windings extends distally from the head when the coil body is compression or press fit with the head.

19. The surgical fastener according to claim 18, wherein the portion of the coil body is located at the proximal end thereof.

20. The surgical fastener according to claim 19, wherein the portion of the coil body includes at least a half turn of a coil winding.

21. The surgical fastener according to claim 18, wherein the cavity of the head receives a proximal portion of the coil body therein to secure the coil body to the head.

22. The surgical fastener according to claim 18, wherein the at least one locking feature includes a recess located on the head and a hook located at the proximal end of the coil body that is engaged with the recess to secure the head to the coil body.

23. The surgical fastener according to claim 18, wherein the at least one locking feature includes an abutment located on the head that is engaged by the proximal end of the coil body to secure the head to the coil body.

24. The surgical fastener according to claim 23, wherein the head includes a guide constructed and arranged to guide the coil body, the abutment being located at an end of the guide.

25. The surgical fastener according to claim 24, wherein the guide is a ramp.

26. The surgical fastener according to claim 18, wherein the coil body is constructed and arranged to mate with a corresponding external thread on a guide rod of a delivery device.

27. The surgical fastener according to claim 18, wherein the at least one drive feature is one or more recesses formed in the head.

28. The surgical fastener according to claim 27, wherein the head includes an outer periphery and the at least one drive feature is located at the outer periphery.

* * * * *

UNITED STATES PATENT AND TRADEMARK OFFICE
CERTIFICATE OF CORRECTION

PATENT NO. : 9,615,830 B2  
APPLICATION NO. : 14/075441  
DATED : April 11, 2017  
INVENTOR(S) : Kevin J. Ranucci et al.

Page 1 of 1

It is certified that error appears in the above-identified patent and that said Letters Patent is hereby corrected as shown below:

In the Claims

At Column 8, Line 56, Claim 10 – after "the" (first occurrence) please insert -- head --

Signed and Sealed this  
Fifth Day of December, 2017

Joseph Matal  
*Performing the Functions and Duties of the*  
*Under Secretary of Commerce for Intellectual Property and*  
*Director of the United States Patent and Trademark Office*